US00PP19439P2

(12) United States Plant Patent
Tristram

(10) Patent No.: US PP19,439 P2
(45) Date of Patent: Nov. 11, 2008

(54) ***HELLEBORUS* PLANT NAMED 'WALHERO'**

(50) Latin Name: ***Helleborus* hybrid**
Varietal Denomination: Walhero

(76) Inventor: David Tristram, Walberton Nursery, Yapton Lane, Walberton, Arundel, BN18 OAS (GB)

( * ) Notice: Subject to any disclaimer, the term of this patent is extended or adjusted under 35 U.S.C. 154(b) by 0 days.

(21) Appl. No.: 11/732,597

(22) Filed: Apr. 3, 2007

(51) Int. Cl.
*A01H 5/00* (2006.01)

(52) U.S. Cl. ..... Plt./439

(58) Field of Classification Search ..... Plt./439
See application file for complete search history.

*Primary Examiner*—Kent L. Bell
*Assistant Examiner*—Georgia Helmer

(57) ABSTRACT

A new cultivar of *Helleborus* named 'Walhero' that is characterized by vigorous growth, early and prolific flowering with saucer-shaped mid to dark pink flowers and medium-green foliage. In combination these traits set 'Walhero' apart from all other varieties of *Helleborus* known to the inventor.

2 Drawing Sheets

Genus: *Helleborus.*
Species: Hybrid.
Denomination: 'Walhero'.

BACKGROUND OF THE INVENTION

The present invention relates to a new and distinct cultivar of *Helleborus* that is grown for use as an ornamental plant for the garden and landscape. The new cultivar is known botanically as *Helleborus* hybrid and will be referred to hereinafter by the cultivar name 'Walhero'.

'Walhero' resulted from a breeding program that was established by the inventor in 1980 in a cultivated area of Sussex, England. The purpose of the breeding program is to produce new *Helleborus* plants exhibiting vigorous growth rates and attractive well-presented flowers. 'Walhero' is a hybrid plant that was selected by the inventor in 2002 for its combination of commercially useful characteristics, including plant form and vigor, crop uniformity, and attractive large nearly flat pink flowers.

Commencing in 1980, the inventor began to assemble a large collection of *Helleborus* plants by raising and crossing promising seedlings. In particular, the inventor included selected seedlings of *Helleborus niger* 'Potter's Wheel' strain (unpatented) which the inventor regarded as having desirable characteristics of vigor, form and presentation of flowers, and these were crossed with selected seedlings of the species *Helleborus orientalis.* Seedlings which resulted from each year's hybridizations were grown to first or second year flowering, and a select number were retained for longer term evaluation. All seedlings were raised and grown on for evaluation and eventual selection in an unheated greenhouse at the inventor's nursery in Sussex, England. The inventor selected 'Walhero' from this population in 2002.

'Walhero' is a perennial plant that exhibits vigorous upright growth, large pink flowers and medium-green leaves. The distinguishing characteristics that make 'Walhero' unique are crop uniformity, vigorous upright growth, prolific flowering and well presented large, saucer-shaped, mid to dark pink flowers that have not been observed to set seed.

The parents of 'Walhero' were an unnamed and unreleased seedling which bore the large white open-faced flowers which are characteristic of *Helleborus niger* 'Potter's Wheel' strain, and an unnamed and unreleased seedling of the species *Helleborus orientalis* which bore light to mid pink colored flowers of average size (diameter approximately 7 cm). By comparison with its parents, 'Walhero' is more vigorous and produces many more flowers whose size, shape and color combine the large open-faced flowers of the 'Potter's Wheel' strain parent with larger and deeper pink colored flowers than the chosen *Helleborus orientalis* parent.

The closest comparison plants in commerce, known to the inventor, are pink-flowered seedling forms of *Helleborus orientalis* and the pinker selections of the normally white *Helleborus niger.*

Walhero is distinguishable from such plants by its vigorous growth, its upright flower stems, its earliness, and its large flowers borne prolifically which are held in a more upright position and are distinctly pink in color throughout its period of flowering.

The first asexual propagation was accomplished by the inventor in 2003 in a cultivated area of Sussex, England. Asexual propagation of the new cultivar 'Walhero' was conducted by the inventor using the method of tissue culture. The unique features of 'Walhero' proved stable and the plant reproduces true to type in successive generations of asexual propagation.

SUMMARY OF THE INVENTION

The following represent the distinguishing characteristics of the new *Helleborus* cultivar 'Walhero'. In combination, these traits set 'Walhero' apart from all other existing varieties of *Helleborus* known to the inventor. 'Walhero' has not been tested under all possible conditions and phenotypic differences may be observed with variations in environmental, climatic, and cultural conditions, however, without any variance in genotype.

1. 'Walhero' grows vigorously and produces a uniform crop.

2. At two years of age, plants of 'Walhero' are approximately 35 cm. in height and 50 cm. in width.
3. The foliage of 'Walhero' is medium-green in color.
4. 'Walhero' produces flowers profusely over a long period, from mid winter and continuing well into spring.
5. The flowers of 'Walhero' are large, saucer-shaped, and are held on upright stems.
6. The flowers of 'Walhero' are mid to dark pink in color.
7. 'Walhero' is hardy in USDA Zone 6.

BRIEF DESCRIPTION OF THE DRAWINGS

The accompanying color drawings illustrate the overall appearance of the new *Helleborus* variety 'Walhero' showing the colors as true as it is reasonably possible to obtain in colored reproductions of this type. Colors in the drawings may differ from the color values cited in the detailed botanical description, which accurately describe the actual colors of the individual plant from which data was collected.

The drawing labeled as FIG. 1 illustrates a three-year old plant in full flower growing outdoors in Sussex, England, in late spring.

Figure 1:
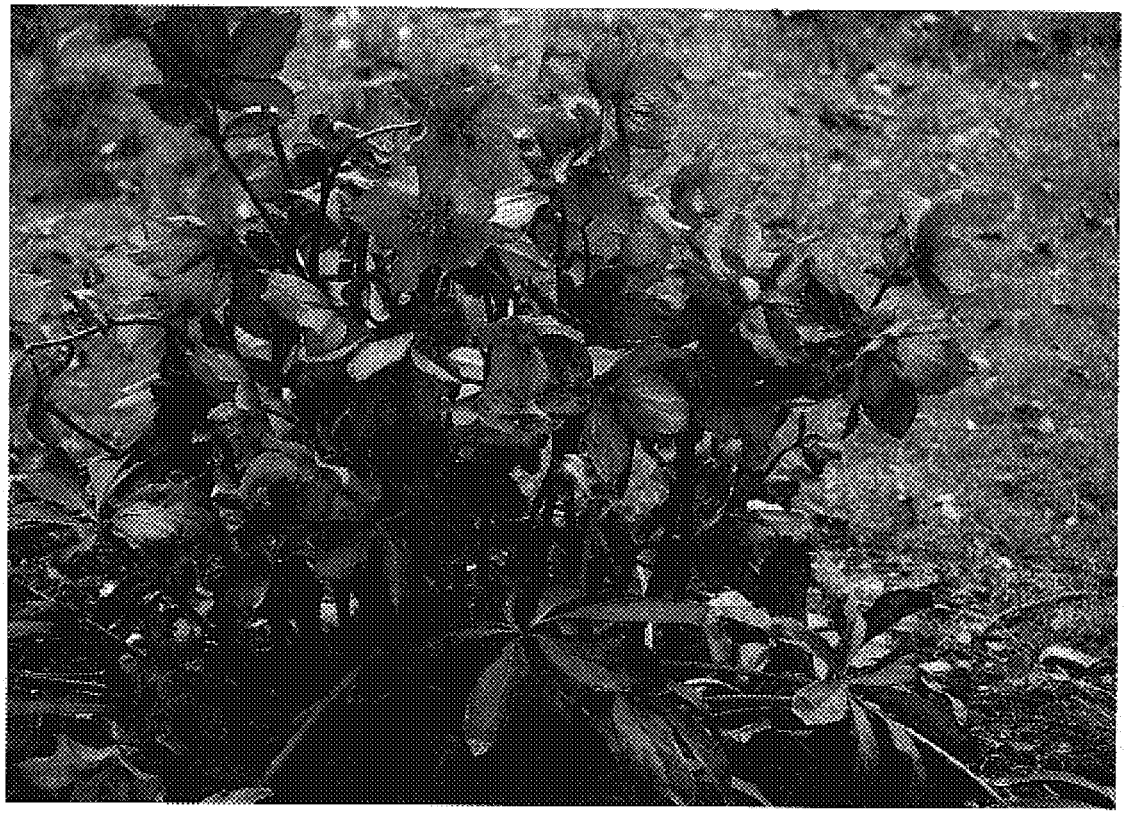
Figure 2:
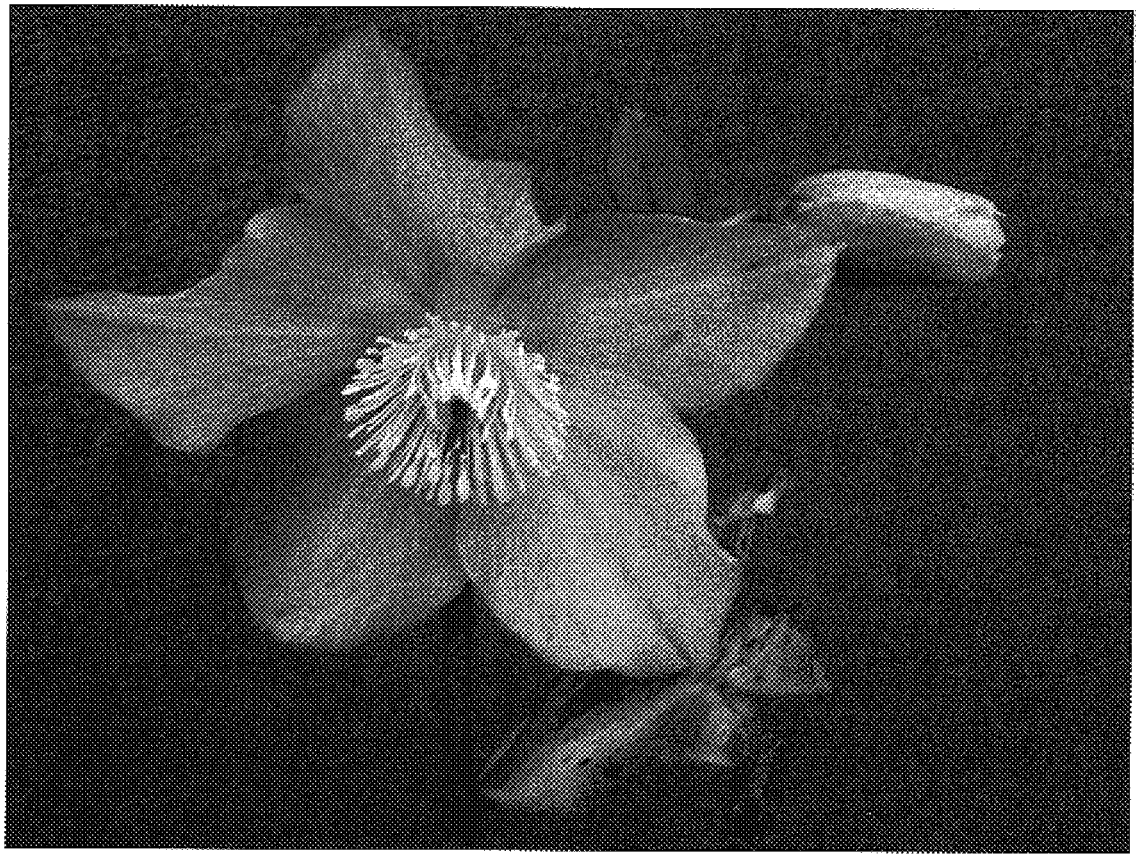

The drawing labeled as FIG. 2 illustrates a close-up view of an individual flower and bud.

All drawings are made using conventional techniques and although foliage colors may appear different from actual colors due to light reflectance, they are as accurate as possible by conventional photography.

BOTANICAL DESCRIPTION OF THE PLANT

The following is a detailed description of the *Helleborus* cultivar named 'Walhero'. Data was collected in Sussex, England from 2-year-old plants grown in 3-liter containers out-of-doors. Color determinations are in accordance with The 2001 Royal Horticultural Society Colour Chart except where general color terms of ordinary dictionary significance are used. The growing requirements are similar to the species.

Botanical classification: *Helleborus* 'Walhero'.
Species: hybrid.
Common name: Hellebore.
Use: Ornamental.
Parentage: 'Walhero' was selected from plants whose parentage includes seedlings of *Helleborus niger,* 'Potters Wheel' strain, and seedlings of the species *Helleborus orientalis.*
Commercial classification: Perennial.
Vigor: Highly vigorous.
Habit: Upright and compact.
Height (at 2 years): 35 cm. in height.
Width (at 2 years): 50 cm. in width.
Hardiness: USDA Zone 6.
Propagation: Tissue culture.
Root system: Fibrous.
Soil: Plant in deep fertile soil that is rich with humus.
Sunlight: Plant in moderate, light or filtered shade.
Time to initiate rooting: 4–6 weeks are needed to produce roots.
Temperature to initiate rooting: Rooting is initiated at 15 degrees Centigrade air temperature.
Crop time: 2 years are needed to produce a finished 3-liter container with flower from a weaned micropropagule.
Seasonal interest: Weather permitting, the first flowers generally open around Christmas and sales are made in January and February when many flowers are open. Flowering continues into March and April.
Disease and pests: Susceptible to *Coniothyrium hellebori* and hellebore aphids.
Other: Living and dried plants are poisonous.
Stem: Acaulescent: leaf and flower stems emerge basally.
Foliage:
*Type.*—Evergreen.
*Leaf arrangement.*—Pedate.
*Leaf division.*—Compound.
*Petiole shape.*—Round with longitudinal groove.
*Petiole color.*—146B.
*Petiole surface.*—Glabrous and fluted.
*Petiole texture.*—Pithy.
*Petiole length.*—The petiole ranges in length from 15 cm. to 25 cm.
*Petiole diameter.*—The diameter of the petiole is 3 mm to 6 mm.
*Leaf dimensions.*—Variable in size between 10 cm in length by 10 cm in width to 25 cm in length by 25 cm in width.
*Number of leaflets* (*per leaf*).—Leaflets range in number from 3–9 leaflets per leaf.
*Leaflet shape.*—Elliptical to lanceolate.
*Leaflet margins.*—Serrate.
*Leaflet apex.*—Acute.
*Leaflet base.*—Cuneate.
*Leaflet surfaces* (*adaxial and abaxial surface*).—Glabrous.
*Leaflet appearance* (*adaxial and abaxial surfaces*).—Semi-glossy.
*Vein pattern.*—Pinnate.
*Vein color* (*abaxial surface*).—191B.
*Vein color* (*adaxial surface*).—191A.
*Leaflet attachment.*—Petiolulate.
*Petiolule surface.*—Glabrous.
*Petiolule dimensions.*—6 mm. in length and 3 mm to 4 mm in diameter.
*Petiolule color.*—199B.
*Petiolule shape.*—Sulcate.
*Leaflet dimensions.*—Leaflet dimensions range from 7–13 cm. in length and 2–5 cm. in width on an individual leaf.
*Leaflet color* (*adaxial surface*).—Individual colors 189A and 191A are both present on an individual leaflet.
*Leaflet color* (*abaxial surface*).—Individual colors 191A and 191B are both present on an individual leaflet.
*Stipules.*—None.
*Foliar fragrance.*—None observed.
Flower:
*Blooming season.*—Winter and early spring.
*Self-cleaning or persistent.*—Persistent sepals and self-cleaning nectaries.
*Inflorescence type.*—Spicate.
*Color of peduncle.*—183B and 195B both present.
*Internode length.*—2–7 cm. in length.
*Peduncle shape.*—Rounded slightly fluted.
*Peduncle length.*—10–30 cm. in length.
*Peduncle width.*—4–6 mm. in width.
*Peduncle surface.*—Glabrous.
*Pedicel color.*—165A.

*Pedicel length.*—Length of pedicels on an individual peduncle can include a range of 2.5–6.0 cm. in length.
*Pedicel diameter.*—2–3 mm. in diameter.
*Pedicel surface.*—Glabrous.
*Diameter of flower.*—8 cm. in diameter, increasing to 10 cm. as the flower ages.
*Depth of flower.*—2 cm. in depth.
*Flower shape.*—Obtusely stellate.
*Aspect.*—Flowers presented horizontally or slightly nodding.
*Petals.*—Present only as nectaries which fall off early while the sepals remain.
*Sepals.*—Five sepals in number.
*Sepal shape.*—Between ovate and orbicular.
*Sepal apex.*—Rounded.
*Sepal base.*—Rounded.
*Sepal surface* (*adaxial and abaxial surfaces*).—Slightly puberulent.
*Sepal margin.*—Entire.
*Sepal color* (*adaxial and abaxial surfaces*).—Individual colors 183D, 186B, 199C and white are all present on an individual sepal over the course of the blooming period.
*Sepal length.*—4.0–4.5 cm. in length, increasing to 4.5–5.0 cm. as the flower ages.
*Sepal width.*—3.0–3.5 cm. in width, increasing to 4.5–5.0 cm. as the flower ages.
*Unfused or fused.*—Sepals are unfused.
*Bud color.*—183C and 186C are individually present on an individual bud.
*Bud shape.*—Nux-shaped.
*Bud dimensions.*—3 cm. in length and 1.5 cm. in width.
*Bracts* (*subtending one bud*).—Leafy bracts may be two or one in number.
*Bract shape.*—Oval.
*Bract attachment.*—Sessile.
*Bract color* (*adaxial surface*).—138B.
*Bract color* (*abaxial surface*).—Colors 138A and 182C may be individually present.
*Bract dimensions.*—1.5–2.0 cm. in width and 2.5–4.0 cm. in length.
*Bract margins.*—Entire.
*Bract apex.*—Acute.
*Bract base.*—Rounded to cuneate.
*Bract surface.*—Glabrous.
*Quantity of flowers.*—Three or four flowers per spike.
*Lastingness of flower.*—An individual flower will last 15 days on the plant and 10 days off the plant, but will retain its shape for two months.
*Fragrance.*—None observed.

Reproductive organs:
*Stamens.*—Number of stamens is approximately 50.
*Color of stamens.*—149D.
*Dimensions of stamen.*—1.0–1.5 cm. in length and 0.5–0.7 mm. in width.
*Dimensions of anther.*—1.5 mm. in width and 2.0–2.5 mm. in length.
*Pollen color.*—154D.
*Amount of pollen.*—Moderate amount.
*Anther color.*—154D.
*Anther shape.*—Elongated disc with longitudinal groove.
*Pistils.*—Five in number.
*Pistil dimensions.*—2 cm. in length and 0.7 mm. in width.
*Pistil shape.*—Group of 5 pistils in fountain-shaped ending in 5 slender tips.
*Pistil color.*—183B.
*Stigma dimensions.*—0.5 mm. in length and 0.5 mm. in width.
*Stigma color.*—154D.
*Nectary.*—12 in number.
*Nectary color.*—N144A.
*Nectary arrangement.*—Whorl.
*Nectary shape.*—Tubular flattened.
*Nectary dimensions.*—7 mm. in length and 3 mm. in width.
*Ovary position.*—Superior.
*Ovary shape.*—Oval.
*Ovary dimensions.*—2 mm. in width and 6 mm. in length.
*Ovary color.*—145B.

Seed: Seed development has not been observed.

What is claimed is:

1. A new and distinct variety of *Helleborus* plant named 'Walhero' as described, and illustrated.

* * * * *